United States Patent
Rapoport

(10) Patent No.: US 10,983,604 B2
(45) Date of Patent: Apr. 20, 2021

(54) FOOT CONTROLLED CURSOR

(71) Applicant: Alcon Inc., Fribourg (CH)

(72) Inventor: Tobias Jura Rapoport, Berlin (DE)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 16/406,315

(22) Filed: May 8, 2019

(65) Prior Publication Data

US 2019/0354201 A1 Nov. 21, 2019

Related U.S. Application Data

(60) Provisional application No. 62/672,347, filed on May 16, 2018.

(51) Int. Cl.
| | | |
|---|---|---|
| *G06F 3/033* | (2013.01) |
| *G16H 40/63* | (2018.01) |
| *G06F 3/01* | (2006.01) |
| *G06F 3/0338* | (2013.01) |
| *G06F 3/0346* | (2013.01) |
| *G06F 3/0354* | (2013.01) |
| *G06F 3/0481* | (2013.01) |
| *G06F 3/0484* | (2013.01) |

(52) U.S. Cl.
CPC ............ *G06F 3/0334* (2013.01); *G06F 3/011* (2013.01); *G06F 3/0338* (2013.01); *G06F 3/0346* (2013.01); *G06F 3/03547* (2013.01); *G06F 3/04817* (2013.01); *G16H 40/63* (2018.01); *G06F 3/04842* (2013.01)

(58) Field of Classification Search
CPC .. G06F 3/0334; G06F 3/0346; G06F 3/04817; G06F 3/03547; G06F 3/0338
See application file for complete search history.

(56) References Cited

U.S. PATENT DOCUMENTS

| 6,091,402 A * | 7/2000 | Howell ................. G06F 3/0334 |
| | | 345/157 |
| 6,659,998 B2 | 12/2003 | Dehoogh et al. |
| 7,127,401 B2 | 10/2006 | Miller |
| (Continued) |

FOREIGN PATENT DOCUMENTS

| EP | 2630930 B1 | 12/2014 |
| WO | WO2004001569 A2 | 12/2003 |
| (Continued) |

*Primary Examiner* — Kent W Chang
*Assistant Examiner* — Scott D Au

(57) ABSTRACT

The present disclosure generally relates to a method for controlling a medical device. The method may comprise tracking movement of a foot with a hands-free device and processing movement of the foot to move a cursor, wherein the cursor is disposed on a display screen of the medical device. The method may further comprise receiving a selection of at least one icon with the cursor through the hands-free device. A system for controlling a medical device may comprise a console and a display screen coupled to the console and may be configured to display a cursor. The system may further comprise a hands-free device. The hands-free device may be communicatively coupled to the console and may be operable to track movement within a tracking area and generate an output. The system may further comprise a medical device connected to the console and a processor configured to execute instructions.

20 Claims, 6 Drawing Sheets

(56) References Cited

U.S. PATENT DOCUMENTS

| | | |
|---|---|---|
| 7,178,111 B2 | 2/2007 | Glein |
| 7,470,277 B2 | 12/2008 | Finlay |
| 8,176,442 B2 | 5/2012 | Poot |
| 8,680,412 B2 | 3/2014 | Horvath |
| 9,240,110 B2 | 1/2016 | Roth |
| 9,256,282 B2 | 2/2016 | Latta |
| 9,681,982 B2 | 6/2017 | Yacono |
| 9,775,682 B2 | 10/2017 | Quaid |
| 9,829,989 B2 | 11/2017 | Mcgrath |
| 9,898,675 B2 | 2/2018 | Yee |
| 9,971,491 B2 | 5/2018 | Schwesinger |
| 9,974,622 B2 | 5/2018 | Franjic |
| 10,222,874 B2 | 3/2019 | Dillon |
| 10,278,782 B2 | 5/2019 | Jarc |
| 10,409,443 B2 | 9/2019 | Wright |
| 10,426,339 B2 | 10/2019 | Papac |
| 10,432,922 B2 | 10/2019 | Jarc |
| 10,492,873 B2 | 12/2019 | Hallen |
| 2004/0161132 A1 | 8/2004 | Cohen |
| 2007/0149956 A1 | 6/2007 | Liedel |
| 2008/0129695 A1* | 6/2008 | Li .................. G06F 3/0334 345/163 |
| 2009/0049397 A1 | 2/2009 | Boukhny |
| 2009/0118714 A1 | 5/2009 | Teodorescu |
| 2009/0171328 A1 | 7/2009 | Horvath |
| 2010/0001948 A1 | 1/2010 | Logue |
| 2010/0013812 A1* | 1/2010 | Gu .................. G06F 3/014 345/207 |
| 2010/0039379 A1* | 2/2010 | Hildreth ............. G06F 3/042 345/156 |
| 2011/0199393 A1* | 8/2011 | Nurse .............. G06F 3/0482 345/665 |
| 2012/0302941 A1 | 11/2012 | Teodorescu |
| 2013/0096575 A1 | 4/2013 | Olson |
| 2014/0313172 A1 | 10/2014 | Moe |
| 2015/0173725 A1 | 6/2015 | Maxson |
| 2015/0182289 A1 | 7/2015 | Itkowitz |
| 2015/0196231 A1 | 7/2015 | Ziaie |
| 2016/0202765 A1 | 7/2016 | Rew |
| 2016/0235489 A1 | 8/2016 | Gombert |
| 2017/0143442 A1 | 5/2017 | Tesar |
| 2017/0364163 A1 | 12/2017 | Tian |
| 2018/0111265 A1 | 4/2018 | Delspina |
| 2018/0132948 A1 | 5/2018 | Mercado |
| 2018/0360653 A1 | 8/2018 | Ren |
| 2018/0280100 A1 | 10/2018 | Reinstein |
| 2019/0361591 A1 | 5/2019 | Zieger |
| 2019/0361592 A1 | 5/2019 | Zieger |
| 2019/0350757 A1 | 11/2019 | Charles |
| 2019/0354200 A1 | 11/2019 | Rapoport |
| 2019/0354201 A1 | 11/2019 | Rapoport |
| 2020/0064879 A1 | 2/2020 | Jawidzik |

FOREIGN PATENT DOCUMENTS

| | | |
|---|---|---|
| WO | WO2011085815 A1 | 7/2011 |
| WO | WO2017110333 A1 | 6/2017 |
| WO | WO2019083805 A1 | 10/2018 |

* cited by examiner

FOOT CONTROLLED CURSOR

BACKGROUND

Surgical operations often require many different and specialized tools. The tools may include a complex machine, designed to function and/or operate in a specific manner. Furthermore, tools may have individual controls that do not communicate and/or work with other controls. Specifically, controls may be in the form of foot pedals, which may allow a surgeon to operate and control a tool with their feet. This presents many challenges in the operating room during a surgical operation.

For example, a medical device, controlled by a foot pedal, may include more functions and/or operations than switches and/or buttons on the foot pedal. To operate and/or function a medical device in a manner not attached to the foot pedal may be performed by an operator utilizing a touch screen to select such operations and/or functions. This may not be possible as the operator may have both hands operating other medical devices, which may be disposed in a patient. Current techniques for controlling the function and/or operation of medical devices during a surgical operation are both rudimentary and onerous and may lead to costly mistakes that a patient may bear.

SUMMARY

In an exemplary aspect, the present disclosure is directed to a method. The method for controlling a medical device may comprise tracking movement of a foot with a hands-free device and processing movement of the foot to move a cursor. The cursor may be disposed on a display screen of the medical device. The method may further include receiving a selection of at least one icon with the cursor through the hands-free device.

In another exemplary aspect, the present disclosure is directed to a system for controlling a medical device. The system may comprise a console and a display screen coupled to the console and may be configured to display a cursor. The system may further comprise a hands-free device. The hands-free device may be communicatively coupled to the console and may be operable to track movement within a tracking area and generate an output. The system may further comprise a medical device connected to the console and a processor configured to execute instructions. The processor may perform the steps to control the cursor according to the output of the hands-free device and receive selection of at least one icon with the cursor by a click through the hands-free device according to the output of the hands-free device.

The different aspects may include on or more of the following features. The method for controlling a medical device may further comprise attaching the medical device to a console, wherein the hands-free device may be communicatively coupled to the console. The method for controlling a medical device may further comprise sending a command to the medical device based on the selection. The hands-free device may be wirelessly attached to a console of the medical device. The selection may control functionality of the medical device. Without limitation the receiving the selection comprises receiving a double click by way of the movement of the foot. The hands-free device may comprise a virtual-foot pedal that captures movement of the foot. The hands-free device may comprise a sensitive surface pad for receiving input from an operator. The hands-free device may comprise a sensitive surface pad and wherein an operator moves the foot across a surface of the sensitive surface pad. The sensitive surface pad may detect a position of the foot from changes in electrical resistance, changes in capacitance, or changes in inductance. The hands-free device may comprise motion hardware and wherein the motion hardware is disposed on the foot of an operator. It should be noted, without limitation the hands-free device is a joystick.

The different aspects may include on or more of the following features. The system for controlling a medical device wherein the hands-free device may comprise a virtual-foot pedal. The hands-free device may comprise a sensitive surface pad and wherein an operator moves the foot across a surface of the sensitive surface pad. Without limitation, the sensitive surface pad is operable to detect position from changes in electrical resistance, changes in capacitance, or changes in inductance. The hands-free device may comprise motion hardware, and wherein the motion hardware is disposable on a foot of an operator. The motion hardware may comprise acceleration sensors, electronic compass, gyro sensors, or position encoders. The display screen may be a touch screen and/or a heads-up display. Without limitation, the at least one icon may be operable to control an operation of the medical device. The at least one icon may be operable to access sub-modes, wherein the sub-modes are operable to control functionality of the medical device.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

These drawings illustrate examples of certain aspects of some of the embodiments of the present disclosure and should not be used to limit or define the disclosure.

DETAILED DESCRIPTION

Figure 1:
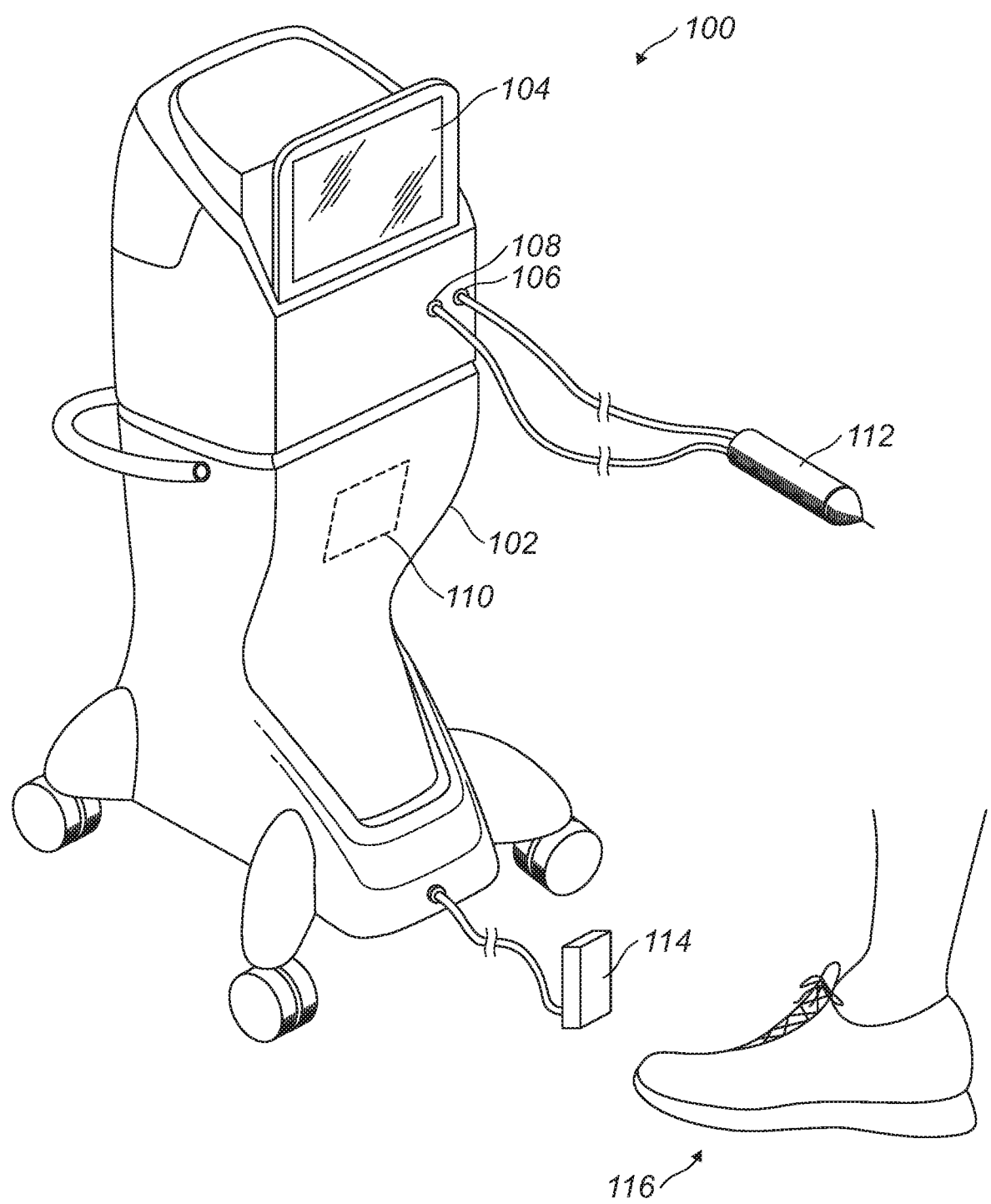
FIG. 1 illustrates an example of console and hands-free device.

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

The present disclosure generally relates to medical device controls for use in an operating room for treatment of a patient (e.g., surgical operations) or in diagnosis. It should be noted that the system disclosed below may be utilized in any type of operation room for any type of medical treatment, including ophthalmic surgical procedures. Due to the nature of the complex workflow during an operation, hands-free control may be desirable. In embodiments, operations may include different hands-free input devices, such as physical foot pedals, virtual-foot pedals, sensitive surfaces, and hardware that may detect motion. Each hands-free device may control any number of surgical devices in the operating room. Hands-free devices may be limited by the number of buttons, joysticks, and/or rockers which may control identified functions on a specific device. Currently, control options may be limited by the number of available buttons and actions that may be assigned to each button disposed on a hands-free device. For example, a button may perform only a single action or at most a few context sensitive options. Thus, a complex sequence may be difficult to implement.

FIG. 1 illustrates a medical device 100 in accordance with example embodiments. However, without limitation, any type of medical device may be used in embodiments disclosed below. In embodiments, medical device 100 may include a console 102 and an instrument 112. Instrument 112 may be any of a variety of medical instruments that may be used in medical applications, such as ophthalmic surgical procedures, including but not limited to, an ophthalmic microscope, a ultrasonic handpiece, a surgery guidance system, an intraoperative diagnostic unit, a vitrectomy instrument, an infusion cannula, intraocular lens (IOL) inserters, a trocar cannula, laser instrumentation, illumination proper (e.g., a chandelier lighting system, an endoilluminator, etc.). In the illustrated embodiment, the instrument 112 may be in the form of an IOL inserter that is hydraulically driven. As illustrated, Console 102 may include a display screen 104, an irrigation port 106, an aspiration port 108, and a hands-free device 114. Hands-free device 114 may be used in place of a foot pedal and may allow an operator to control the function of attached device without physical switches, buttons, triggers, touchscreen elements, keyboards, mice, and others. In embodiments, console 102 may be designed to be mobile and may be used by a user, such as a health care provider, to perform ophthalmic surgical procedures. Console 102 may also include a control system 110 that may be configured to process, receive, and store data to perform various functions associated with instrument 112.

Display screen 104 may communicate information to the user, and in some implementations, may show data relating to system operation and performance during a surgical procedure. In some embodiments, display screen 104 may be a touchscreen that allows the operator to interact with console 102 through a graphical user interface.

In some embodiments, console 102 may include various fluid handling systems for use during various ophthalmic surgical procedures. In the illustrated embodiment, console 102 may provide irrigation fluid through irrigation port 106. Console 102 may include a pump that can create a vacuum or suction force that may aspirate fluid and tissue through aspiration port 108. In some embodiments, the instrument 112 may use these or other fluid handling systems to drive the instrument 112. Specifically, the instrument 112 may be connected to irrigation port 106 through an irrigation line and may be connected to aspiration port 108 through an aspiration line. While the preceding description is directed to console 102 being configured for use with instrument 112 in the form of an IOL inserter, it should be understood that the present disclosure should encompass other configurations of console 102 depending, for example, on the particular application.

Hands-free device 114 may be described as device for capturing motion of a foot. The hands-free device 114 may enable control of a cursor (e.g., cursor 1002 on FIG. 10), which may be displayed, for example on display screen 104. It should be noted that display screen 104 may include a heads up display. A heads up display may be a transparent display that may present data without requiring an operator to look away from the operator's viewing area. Currently, a foot pedal may perform mechanical movement through physical switches, buttons, triggers, touchscreen elements, keyboards, mice, and others. Each one of these mechanical movements may control a function and/or operation of a device attached to the foot pedal. Foot pedals may be limited by the number of mechanical movements that may be disposed on the foot pedal. Thus, during operations any number of foot pedals may be utilized to control any number of specific and individual devices. Large numbers of foot pedals in an operation may become cumbersome and may lead accidental use of foot pedals that may be in close proximity to each other. Due to space limitations, large numbers of foot pedals may not be feasible. Additionally, foot pedals may be limited by the number of functions they may be able to perform. Thus, to perform more functions may require larger number of foot pedals. A single device, such as hands-free device 114, may declutter the operating room and may prevent unintended function and operation of devices.

In embodiments, hands-free device 114 may track the movement of at least a portion of an operator's foot 116. It should be noted that hands-free device 114 may track the movement of at least a portion of any part of the body designed to work with hands-free device 114. Without limitation, hands-free device 114 may register the position and/or movement of operator's foot 116 through the recognition of the rotation (pitch, yaw, and roll) of foot 116. Measuring the positions and/or movement of foot 116 may allow medical device 100 to identify and determine operation and function of a device. For example, the position of foot 116 and a pre-determined movement of foot 116 in that position may operate and function a first device. A second position of foot 116 and a second pre-determined movement of foot 116 may operate and function a second device.

This may allow hands-free device 114 to control any number of devices and perform any number of functions and/or operations on those devices. Utilizing hands-free device 114 to control any number of device and perform any number of function and/or operations may declutter the operating room and may prevent the accidental use of devices during a surgical operation. Hands-free device 114 may be able to control the function and/or operation of other devices through position tracking. Position tracking may be performed by any number of sensors. Without limitation, position tracking sensors may include optical sensors, acoustic sensors, magnetic sensors, and/or thermal sensors. It should be noted that different types of sensors may work together in a system to form hands-free device 114. Position tracking sensors may also include many different individual devices that may work together to track the movement of foot 116.

Figure 2:
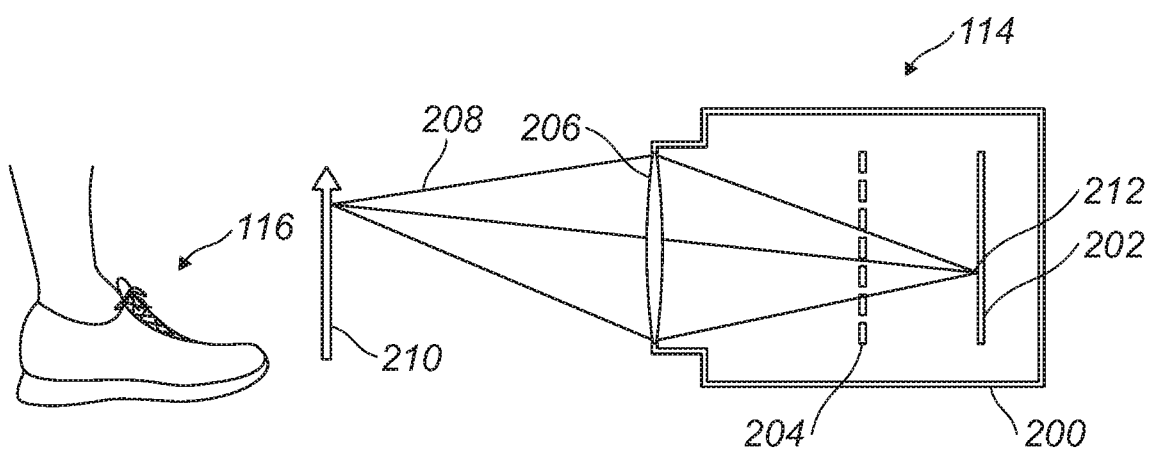
FIG. 2 illustrates an example of an optical tracking device.
Figure 3:
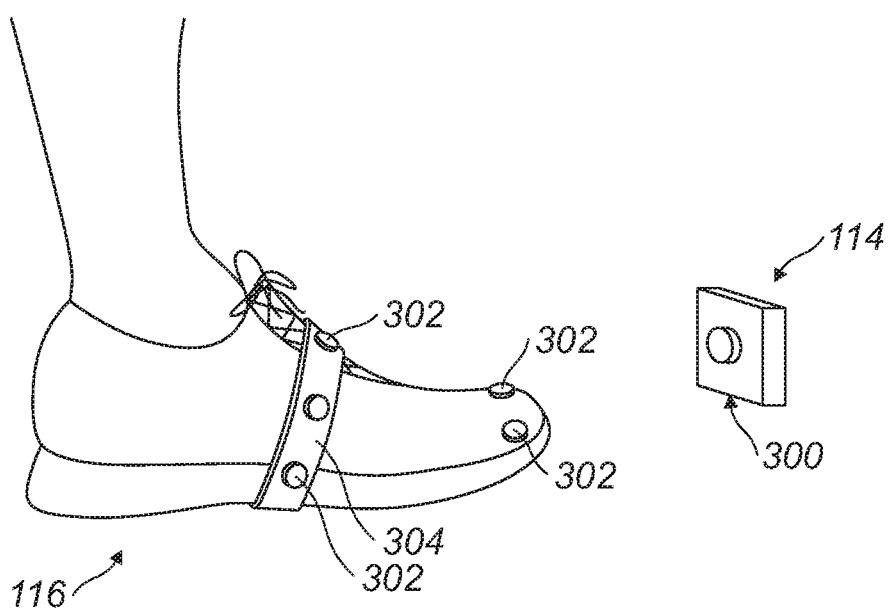
FIG. 3 illustrates another example of an optical tracking device.

FIGS. 2 and 3 illustrates two different devices for optical tracking in accordance with embodiments of the present disclosure. In FIG. 2, hands-free device 114 may include a camera 200 to track the position and movement of foot 116. Disposed in camera 200 may be a sensor 202. Sensor 202 may be sensitive to the intensity of light as sensed across the face of sensor 202. Additionally, camera 200 may comprise a mask 204. Mask 204 may be disposed within camera 200, as illustrated in FIG. 2, disposed along sensor 202, and/or along lens 206. During operations, camera 200 may be exposed to light 208 reflected off foot 116. As foot 116 moves along any axis 210, light 208 reflected from foot 116 may pass through lens 206 and into camera 200. It should be noted that light 208 may also pass through mask 204, which may be disposed at any suitable location in camera 200, as disclosed above. Light 208 passing through lens 206 is deflected and is disposed at a focal point 212 on sensors 202. During movement of foot 116, light 208 may be reflected into camera 200 at different angles. As the angle changes, focal point 212 may move along the face of sensors 202. As the focal point 212 moves, the movement of foot 116 may be tracked and/or recorded on medical device 100 (e.g., referring to FIG. 1). Additionally, camera 200 and/or multiple cameras may capture an image at different times and measure the movement of an object in the image. For example, camera 200 or a plurality of cameras may capture an object in a first image and capture the objection in a second image within seconds of the first image. Camera 200 may be able to determine the movement of an object in the images. This may allow the cameras to operate without continuously capturing images, which may save computing power, reduce data, and save energy. This type of optical tracking may be defined as markerless tracking and/or passive tracking.

FIG. 3 illustrates optical tracking that may be defined as marker tracking and/or active tracking in accordance with embodiments of the present disclosure. In embodiments, hands-free device 114 may include camera 300 that may be designed to record the position and/or movement of markers 302. Markers 302 may comprise any material suitable to reflect visible light and/or infrared light, which may be captured and/or recorded by camera 300. In embodiments, makers 302 may emit visible light and/or infrared light, which may also be captured and/or recorded by camera 300. In examples, there may be at least one marker 302 disposed on foot 116. Without limitation, markers 302 may be disposed on foot 116 at any suitable location and/or may attach to foot 116 through any suitable connector 304. During operation, camera 300 may be disposed in any suitable location to view, capture, and/or record markers 302. Before a surgical operation may begin, camera 300 may calibrate in reference to foot 116 to determine a starting position. During surgical operations, as foot 116 moves, camera 300 may capture, record, and/or track the movement of markers 302 from a first position to a second position. The captured movements of markers 302, which in turn is foot 116, may be tracked and/or recorded on medical device 100 (e.g., referring to FIG. 1).

Figure 4:
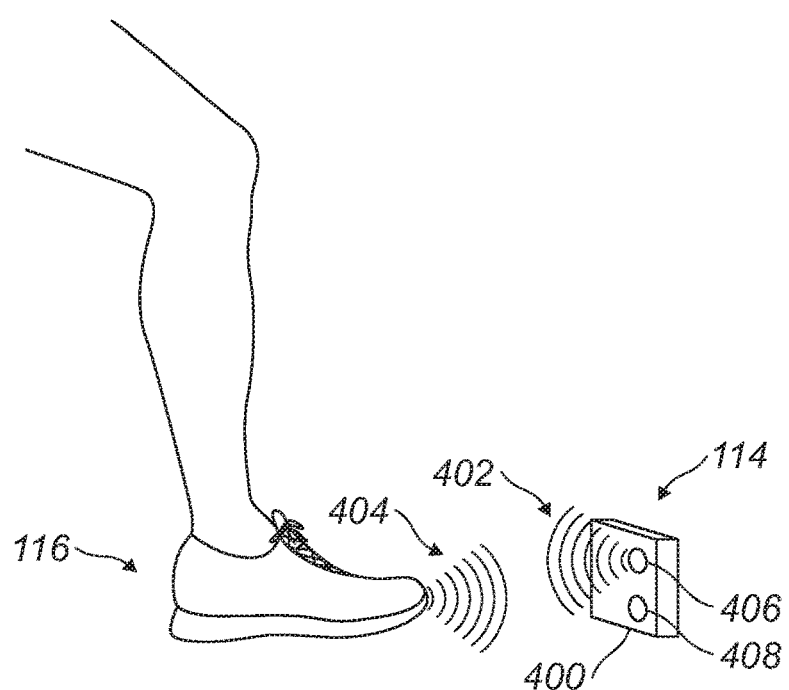
FIG. 4 illustrates an example of an acoustic tracking device.

FIG. 4 illustrates an acoustic tracking device 400 in accordance with embodiments of the present disclosure. In embodiments, hands-free device 114 may include acoustic tracking device 400. There may be any number of suitable acoustic tracking devices 400 operating and/or functioning together to determine the movement and/or position of foot 116. Acoustic tracking device 400 may operate by emitting low frequency and/or high frequency sound waves 402, which may not be heard by humans. In embodiments, different types of sound waves 402 may be emitted concurrently and/or in a pre-determined structure by acoustic tracking device 400. Sound waves 402 may be emitted by a speaker 406 disposed at any suitable location on acoustic tracking device 400. As the sound waves 402 strike foot 116, reflected waves 404 may be sent back toward acoustic tracking device 400 and recorded. As illustrated, acoustic tracking device 400 may include one or more sensors 408 for recording reflected waves 404. Reflected wave s404 may be considered an echo. As foot 116 moves, reflected waves 404 may be altered due to the distance and location of foot 116 in relation to acoustic tracking device 400. This may allow acoustic tracking device 400 to determine the location and position of foot 116. The movement of foot 116 may be tracked and/or recorded on medical device 100 (e.g., referring to FIG. 1).

Figure 5:
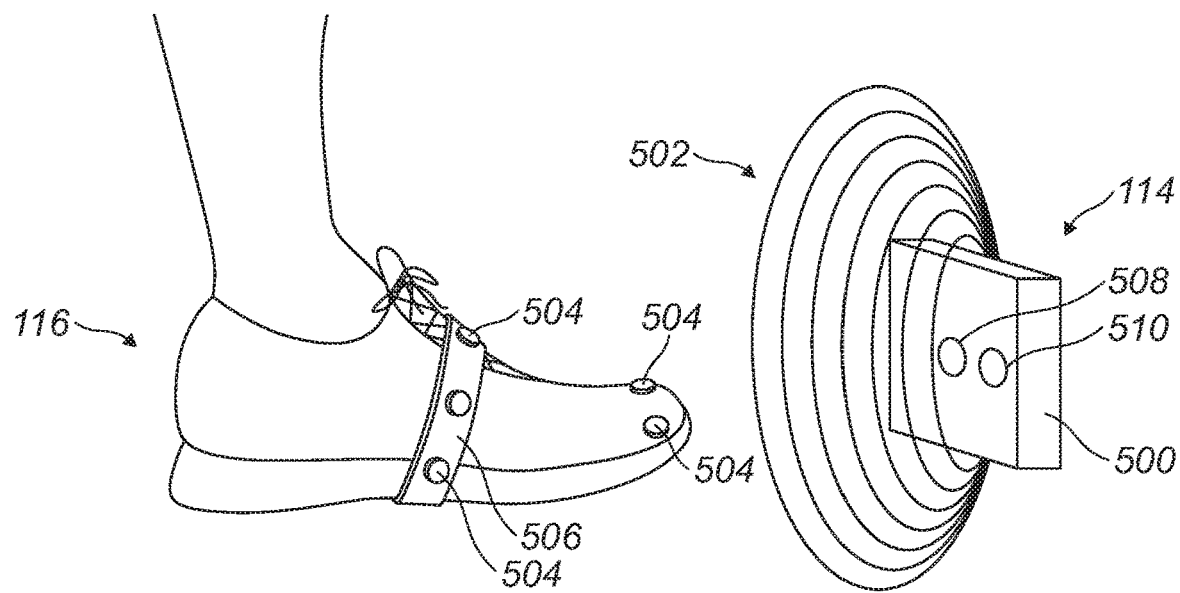
FIG. 5 illustrates an example of a magnetic tracking device.

FIG. 5 illustrates a magnetic tracking device 500 in accordance with embodiments of the present disclosure. In embodiments, hands-free device 114 may include a magnetic tracking device 500. There may be any number of suitable magnetic tracking devices 500 operating and/or functioning together to determine the movement and/or position of foot 116. Magnetic tracking device 500 may operate by emitting an electromagnetic field 502 from a transmitter 508, which may be disposed on or in magnetic tracking device 500. Before operations, magnetic tracking device 500 may be calibrated to determine a base for electromagnetic field 502. A receiver 510 disposed on or in magnetic tracking device 500, may be able to sense electromagnetic field 502 and changes in electromagnetic field 502. In embodiments, magnets 504 may be disposed on foot 116. Magnets 504 may alter electromagnetic field 502. Without limitation, magnets 504 may be disposed individually on foot 116 and/or on a separate holding apparatus 506, which may attach to foot 116 in any suitable manner. In the illustrated embodiment, holding apparatus 506 is in the form of a band. By altering electromagnetic field 502 with magnets 504, the receiver 510 may be able to determine the location and/or position of foot 116. As foot 116 moves, electromagnetic field 502 may be altered due to the distance and location of foot 116 in relation to magnetic tracking device 500. It should be noted that magnets may not be used to alter electromagnetic field 502. Foot 116 may alter electromagnetic field 502 individually, for example, due to iron disposed in blood, or any other type of metal item, device, material, or the like disposed on foot 116 may alter electromagnetic field 502 without the use of magnets 504. This may allow magnetic tracking device 500 to determine the location and position of foot 116. The movement of foot 116 may be tracked and/or recorded on medical device 100 (e.g., referring to FIG. 1).

Figure 6:
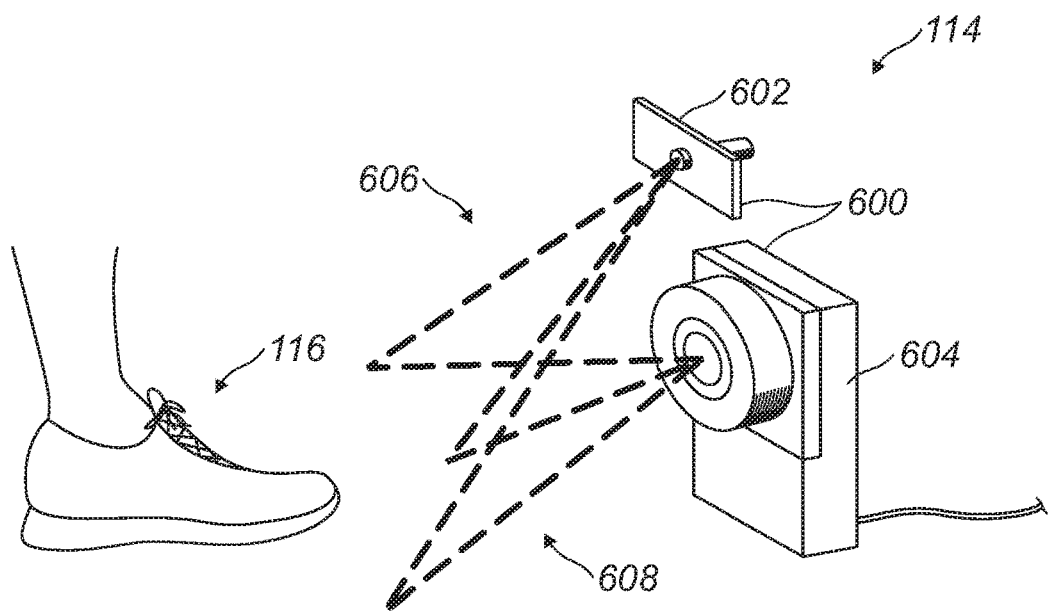
FIG. 6 illustrates an example of an infrared tracking device.

FIG. 6 illustrates an infrared tracking device 600 in accordance with embodiments of the present disclosure. In embodiments, hands-free device 114 may include an infrared tracking device 600. In embodiments, infrared tracking device 600 may comprise a light source 602 and a camera 604. Infrared tracking device 600 may function by emitting non-visible light 606 from light source 602. Non-visible light 606 may comprise infrared wavelengths on the light spectrum. This may allow infrared tracking device 600 to operate in a dark room and/or a lighted room. During operations, light source 602 may emit non-visible light 606 into a designated area. Foot 116 may be disposed in the path of non-visible light 606, which may produce a reflected light 608. Reflected light 608 may be recorded by camera 604. As foot 116 moves from one position to a second position, reflected light 608 may be altered and recorded by camera 604. This may allow infrared tracking device 600 to determine the locations and position of foot 116. The movement of foot 116 may be tracked and/or recorded on console 102 (e.g., referring to FIG. 1).

It should be noted, that in embodiments tracking devices may be able to track light on the visible spectrum. This operation may described as motion tracking, time of flight, or video tracking. Without limitations, motion tracking or video tracking may utilize a single camera and/or multiple cameras working together. By detecting the movement of light across the lens of one and/or a plurality of camera. Tracking the movement of an operators foot 116 may be translated into user input which may be feed into console 102

Figure 7:
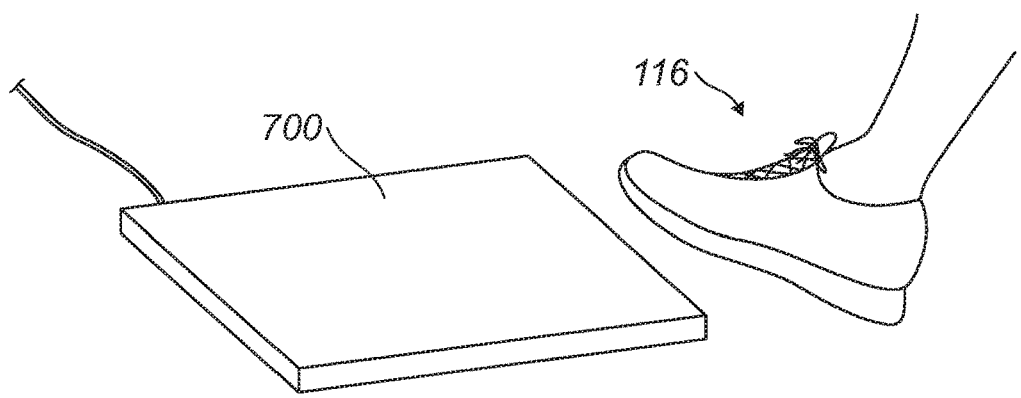
FIG. 7 illustrates an example of a sensitive surface pad.

FIG. 7 illustrates embodiments in which a sensitive surface pad 700 may control a user input into console 102 (e.g., referring to FIG. 1). Sensitive surface pad 700 may be disposed below an operator during a surgical procedure. Without limitations, sensitive surface pad 700 may be able to detect changes in pressure, resistance, capacity, and/or induction. For example, an operator may touch sensitive surface pad 700 with foot 116. Sensitive surface pad 700 may detect the pressure exerted on sensitive surface pad 700 from foot 116 through pressure sensors. In other embodiments, electrical means may be utilized to detect pressure change, and/or movement across sensitive surface pad 700. For example, changes in electrical resistance across sensitive surface pad 700 may be measured, changes in capacitance, and/or changes in inductance may be measured to track movement of foot 116 across sensitive surface pad 700. It should be noted that sensitive surface pad 700 may function and/or operate without pressure being applied as it may only sense change in electrical potential moving across the surface. This may allow sensitive surface pad 700 to determine position and movement of the position across sensitive surface pad 700.

It should be noted that other physical and mechanical devices may be used to control a user input into console 102 (e.g., referring to FIG. 1). For example, a mechanical embodiment such as a joystick controller may be a mechanical device that controls a user input. In embodiments, the joystick controller may include a base, a shaft, and a handle. The base may be disposed on a surface to hold the joystick controller in place. The shaft may be attached to the based in move in any direction within a three hundred and sixty degree radius. The handle may be disposed at the top of the shaft opposite the base. Without limitation, the handle may allow an operator to move the shaft in any suitable direction. Movement of the shaft may be monitored and transmitted to console 102 as user input. Specifically, movement of the shaft may move a cursor, discussed below, disposed on display screen 104 (e.g., referring to FIG. 1).

Figure 8:
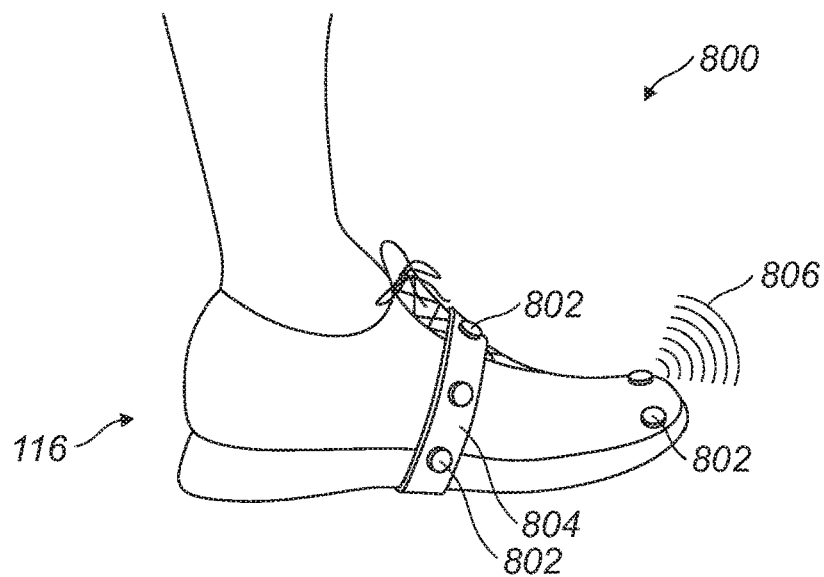
FIG. 8 illustrates an example of motion hardware.

FIG. 8 illustrates an embodiment in which motion hardware 800 may control a user input into console 102 (e.g., referring to FIG. 1). In embodiments, motion hardware 800 may comprise motion detectors 802 which may be secured directly to foot 116 and/or carriers 804. Without limitation, motion detectors 802 may include acceleration sensors, electronic compass, gyro sensors, position encoders, and/or the like. In embodiments, motion detectors 802 may wirelessly transmit communications 806 to console 102. While not shown, motion detectors 802 may alternatively transmit communications 806 to the console 102 via a wired connection. Information received by console 102 from motion detectors 802 may allow for console 102 to track the movement of foot 116. Tracking the movement of foot 116 may allow an operator to communicate with surgical devices (e.g., instrument 112 on FIG. 1) attached to console 102. It should also be noted that this may allow foot 116 to communicate with console 102.

Figure 9:
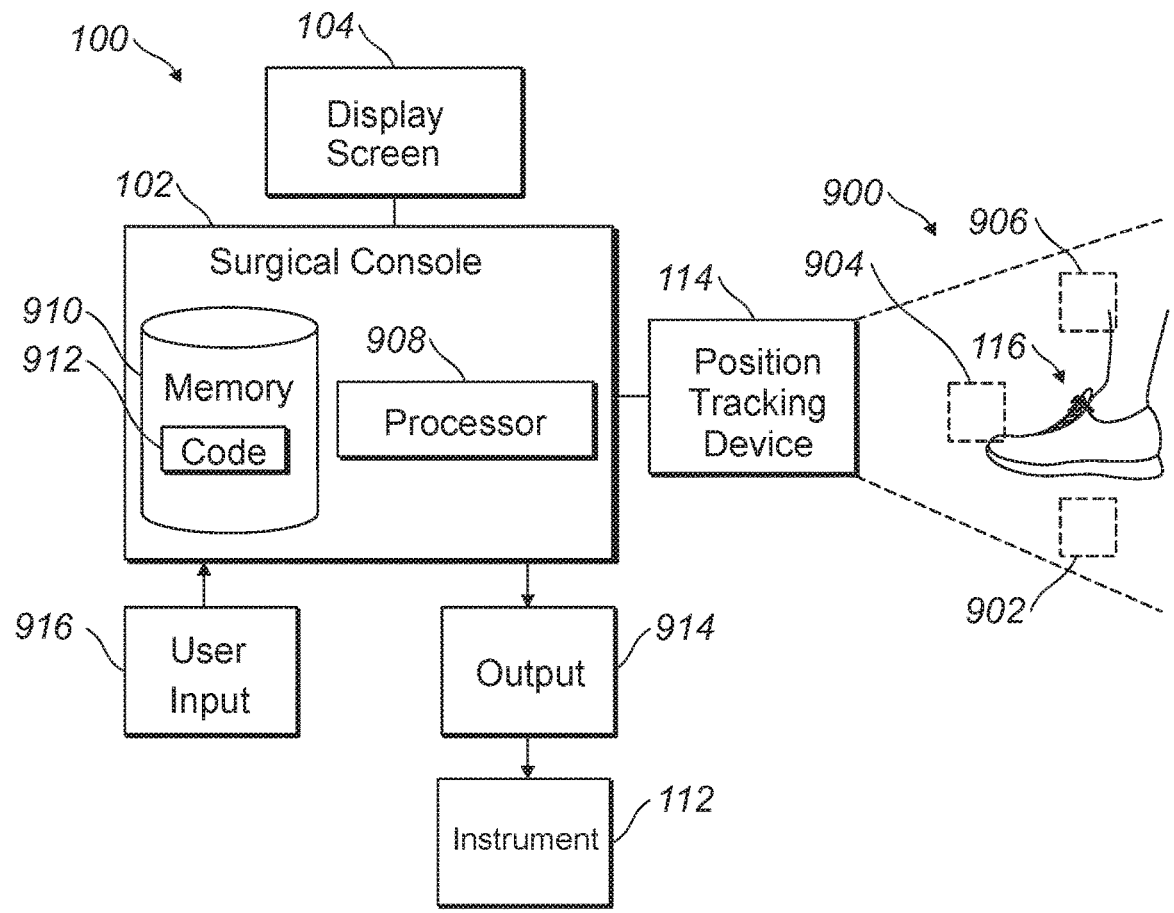
FIG. 9 illustrates a schematic layout of a console and hands-free device.

FIG. 9 illustrates an example of a medical device 100 for recording and/or tracking the movement and/or position of foot 116 with hands-free device 114 in accordance with embodiments of the present disclosure. As discussed above, hands-free device 114 may include any suitable device that may be able to locate and track foot 116 with any suitable technology. It should be noted that hands-free device 114 may be calibrated to operate and/or function in tracking area 900. Tracking area 900 may be a designated area in which hands-free device 114 may operate. For example, if foot 116 is outside tracking area 900, then hands-free device 114 may not record and/or track foot 116. It should be noted, that hands-free device 114 may record and/or track foot 116 outside of tracking area 900 but the movements may be disregarded by medical device 100. This may allow an operator to move foot 116 outside of tracking area 900 and prevent medical device 100 from operating a surgical device.

Console 102 may include a processor 908. Processor 908 may include any suitable device for processing instructions, including, but not limited to, a microprocessor, microcontroller, embedded microcontroller, programmable digital signal processor, or other programmable device. The processor 908 may also, or instead, be embodied in an application specific integrated circuit, a programmable gate array, programmable array logic, or any other device of combinations of devices operable to process electric signals. Processor 908 may also, or instead, be embodied in an application specific integrated circuit, a programmable gate array, programmable array logic, or any other device or combinations of devices operable to process electric signals. Processor 908 may be communicatively coupled to console 102. The connection between processor 908 and console 102 may be a wired connection or a wireless connection, as desired for a particular application. Processor 908 may be configured to receive user inputs 916, for example, to start and/or to stop the operation and/or function of instrument 112.

Console 102 may also include a memory 910, which may be internal or external, for example. Memory 910 may include any suitable form of data storage, including, but not limited to, electronic, magnetic, or optical memory, whether volatile or non-volatile. Memory 910 may include code 912 including instructions that may be executable by processor 908. Code 912 may be created, for example, using any suitable programming language, including but not limited to, C++ or any other programming language (including assembly languages, hardware description languages, and database programming languages) that may be stored, compiled, or interpreted to be executable by processor 908.

In operation, console 102 may receive the information about movement and/or position of foot 116 from hands-free device 114. For example, movement of foot 116 may be recorded and/or tracked by hands-free device 114, this information may be sent to console 102. The position of the foot from hands-free device 114 may be visualized on display screen 104, which may be a heads-up display or monitor. Display screen 104 may also provide feedback to the operator required to keep track of the current status and control options. Console 102 may receive input information from hands-free device 114, which may then be processed by processor 908. While not shown, processor 908 (or a different processor) may alternatively be integrated into hands-free device 114 so that processed data may be provided to console 102. Processor 908 may also receive information from user input 916. The information from the user input 916 may be in addition, or in place of, the information from hands-free device 114. Processor 908 may then process the information, from hands-free device 114, user input 916, or both hands-free device 114 and user input 916, to produce an output 914.

Output 914 may be defined as a set of commands that may be sent to an instrument 112. Commands in output 914 may direct instrument 112 to perform certain functions related to the surgical operation taking place. Instruction may be a simple as turning a light on and/or off or as complex as using instrument 112 on a patient. Commands in output 914 may originate from the movement of foot 116 or user input 916. The movement of foot 116 may be captured, for example, and used to control a cursor (e.g., cursor 1002 shown on FIG. 10) on the display screen 104. As used herein, the term "cursor" refers to a moveable indicator on a display, such as the display screen 104, identifying the current position for user interaction with the display. The cursor may be used make selections for control of instrument 112. The selections may be the set of commands sent to instrument 112 as output 914. User input 916 may be functions and/or commands selected by an operator through display screen 104, for example, by touch.

Figure 10:
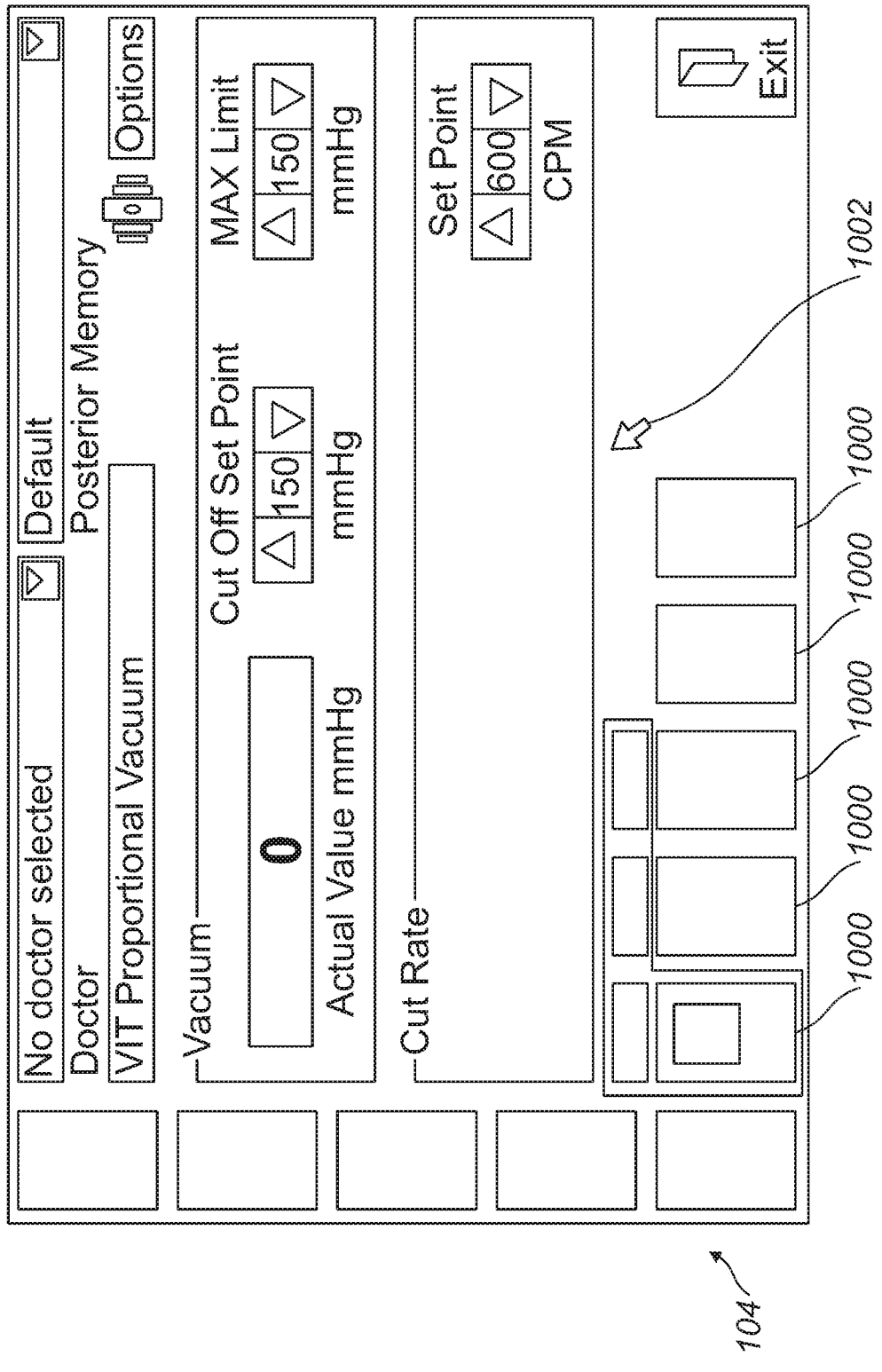
FIG. 10 illustrates an example of a display screen.

As illustrated in FIG. 10, display screen 104 may display patient information and/or status of instrument (e.g., referring to FIG. 7). Display screen 104 may comprise a Graphical User Interface (GUI), which may be displayed on display screen 104, such that an operator may interact with console 102 (e.g., referring to FIGS. 1 and 7). In one embodiment, the GUI for medical device 100 may allow an operator to modally interact with console 102. In other words, the GUI may present an operator of console 102 a set of icons 1000 or buttons corresponding to the entire range of functionality of console 102 or instrument 112 connected to console 102. Display screen 104 may allow an operator to select from these function icons 1000 in order to utilize a particular functionality of console 102 or instrument 112. For example, an operator may use foot 116 (e.g., Referring to FIG. 9) to select a surgical device through cursor 1002. Cursor 1002 may move as directed by an operators' foot 116 as foot 116 is tracked in tracking area 900 (e.g., Referring to FIG. 9). Foot 116 disposed in the tracking area 900 tied to cursor 1002 may allow the operator to move cursor 1002, which may allow the operator to select different function on display screen 104.

For example, cursor 1002 may traverse across display screen 104 as controlled by foot 116 (e.g., referring to FIG. 1) of the operator, which may correspond to the output of hands-free device 114. While cursor 1002 is shown on FIG. 10 as an arrow, cursor 10012 may have any suitable shape, including, but not limited to, an arrow, a pointing finger, or a circle, among others. In embodiments, cursor 1002 may trigger operations and/or functions of instrument 112, which may be represented by a graphical element on display screen 104, for example icons 1000. Cursor 1002 may "click" on icon 1000 to trigger operations and/or function of instrument 112. The term "click" may be defined as placing cursor 1002 over icon 1000 and commanding cursor 1002 from hands-free device 114 to select an icon 1000 in which cursor 1002 may be disposed. Without limitation, different types of clicks may trigger different actions, such as a single click may perform one function and a two successive clicks may perform a different function. This may be repeated for any number of clicks.

Without limitations, icons 1000 may be tied to an instrument 112. To access icons 1000 an operator may dispose foot 116 into a first zone 902, second zone 904, or third zone 906 that may be tied to an icon 1000. Icon 1000 may further be tied to an instrument 112. This may allow operator to dispose foot 116 into the designated zone and issue commands through output 914 (e.g., referring to FIG. 7) to control instrument 112. Selecting icon 1000 may alter display screen 104 by displaying a sub-command that may be specific to the selected instrument 112.

The operator may then configure any parameters or sub-modes for the desired functionality and utilize this functionality on instrument 112. Thus, during a surgical procedure, for each instrument 112 utilized in a surgical procedure an operator may interact with console 102 through hands-free device 114 or user input 916 to select the functionality desired for a surgical procedure and configure any parameters or sub-modes for instrument 112. For example, console 102 and/or instrument 112 may include functionality for vitreous cutting (Vit), vacuum (Extraction), Scissors, Viscous Fluid Control (VFC) and ultrasonic lens removal, an ophthalmic microscope, an ultrasonic handpiece, a surgery guidance system, and/or an interaoperative diagnostic unit. To implement a surgical procedure through console 102 and/or instrument 112, icon 1000 may represent functionality desired of console 102 and/or instrument 112, and any parameters or sub-modes for that functionality configuration.

More specifically, embodiments of modes of interaction with a console 102 may be provided such that these modes of interaction limit or curtail the range of functionality which may be adjusted. In particular, certain embodiments may present one or more interfaces for operator interaction which may allow an operator to select from a set of pre-programmed options, where the interface or the set of preprogrammed options, icons 1000, may correspond to the mode in which an operator may be interacting with console 102. Each of these preprogrammed options may correspond to settings for one or more parameters. By allowing an operator to select from a variety of preprogrammed options, the potential for mistakes and injury are reduced as the settings for each of the preprogrammed options may ensure that the settings for each of the parameters are proper relative to the settings for the other parameters and may similarly ensure that the values for certain parameters may not be set outside of a certain range. Additionally, as the set of parameters are adjusted in tandem according to preprogrammed settings, the interface for a particular mode of operation may be dramatically simplified relative to an interface which forces a doctor to adjust individually each parameter.

In embodiments, display screen 104 may be a touch screen, which may allow an operator to select icons 1000 as user input 916 (e.g., referring to FIG. 9). Specifically, the operator may select a mode of operation and/or instrument 112 by touching display screen 104. Based upon the mode of operation and/or instrument 112 selected, the GUI may present interface which presents an operator with the values of the current settings of a set of parameters. The interface may allow an operator to easily cycle through the set of preprogrammed options, for example by using a touch screen, hands-free device 114, and/or the like, and reflects changes to the settings of the parameters displayed which correspond to the currently selected preprogrammed option.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. A method for controlling at least two medical devices coupled to a surgical console, comprising:
    tracking movement of a foot with a camera;
    processing movement of the foot to move a cursor, wherein the cursor is disposed on a display screen of the surgical console;
    receiving an indication that the foot has entered a first zone of at least two zones, each of the at least two zones associated with a different medical device;
    for the medical device associated with the first zone, presenting to the user on the display screen a first plurality of icons, wherein the first plurality of icons each represent a different pre-programmed option that correspond to different settings for one or more parameters of the medical device associated with the first zone;
    receiving a selection of at least one icon of the first plurality of icons with the cursor through movement of the foot detected by the camera;
    configuring the associated medical device according to the settings for the one or more parameters associated with the pre-programmed option represented by the selected icon; and
    detecting movement of the foot into a second zone of the at least two zones, and presenting to the user on the display screen a second plurality of icons, wherein the second plurality of icons each represent a different pre-programmed option that correspond to different settings for one or more parameters of the medical device associated with the second zone.

2. The method of claim 1, wherein the camera is communicatively coupled to the console.

3. The method of claim 1, further comprising sending a command to the associated medical device based on the icon selection.

4. The method of claim 1, wherein the camera is wirelessly attached to the console.

5. The method of claim 1, wherein the selection controls functionality of the associated medical device.

6. The method of claim 1, where the receiving the selection comprises receiving a double click by way of the movement of the foot.

7. The method of claim 1, wherein tracking movement of the foot with the camera comprises measuring movement of an object in a sequence of images captured by the camera.

8. The method of claim 1, wherein tracking movement of the foot with the camera comprises:
    detecting a focal point of light received by the camera from the foot; and
    detecting movement of the focal point along sensors in the camera.

9. The method of claim 8, wherein the light received by the camera from the foot is light reflected by the foot.

10. The method of claim 8, wherein the light received by the camera from the foot is light from a marker located on the foot.

11. The method of claim 8, wherein the light received by the camera is infrared light.

12. A system for controlling at least two medical devices comprising:
    a console;
    a display screen coupled to the console and configured to display a cursor;
    a camera, wherein the camera is communicatively coupled to the console and is operable to track movement within a tracking area and generate an output;
    at least two medical devices connected to the console;
    a processor configured to execute instructions to:
        control the cursor according to the output of the camera; and
        receive an indication that a foot has entered a first zone of at least two zones, each of the at least two zones associated with a different medical device;
        for the medical device associated with the first zone, present to a user on the display screen a first plurality of icons, wherein the first plurality of icons each represent a different pre-programmed option that correspond to different settings for one or more parameters of the medical device associated with the first zone;
        receive selection of at least one icon of the first plurality of icons with the cursor by a click through the camera according to the output of the camera;
        configure the associated medical device according to the settings for the one or more parameters associated with the pre-programmed option represented by the selected icon; and
        detect movement of the foot into a second zone of the at least two zones, and presenting to the user on the display screen a second plurality of icons, wherein the second plurality of icons each represent a different pre-programmed option that correspond to different settings for one or more parameters of the medical device associated with the second zone.

13. The system of claim 12, wherein the display screen is a touch screen and/or a heads-up display.

14. The system of claim 12, wherein the at least one icon is operable to control an operation of the associated medical device.

15. The system of claim 12, wherein the at least one icon is operable to access sub-modes, wherein the sub-modes are operable to control functionality of the associated medical device.

16. The system of claim 12, wherein tracking movement within the tracking area by the camera comprises measuring movement of an object in a sequence of images captured by the camera.

17. The system of claim 12, wherein tracking movement within the tracking area by the camera comprises:
    detecting a focal point of light received by the camera from the foot; and
    detecting movement of the focal point along sensors in the camera.

18. The system of claim 17, wherein the light received by the camera from the foot is light reflected by the foot.

19. The system of claim 17, wherein the light received by the camera from the foot is light from a marker located on the foot.

20. The system of claim 17, wherein the light received by the camera is infrared light.

* * * * *